United States Patent
Froehlich et al.

(10) Patent No.: US 7,236,912 B2
(45) Date of Patent: Jun. 26, 2007

(54) METHOD AND DEVICE FOR DETERMINING AND/OR MONITORING A VOLUME AND/OR MASS FLOW

(75) Inventors: Thomas Froehlich, Münchenstein (CH); Harald Stocker, Schopfheim (DE); Aurèle Fleury, Aesch (CH)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 10/535,675

(22) PCT Filed: Nov. 17, 2003

(86) PCT No.: PCT/EP03/12860

§ 371 (c)(1),
(2), (4) Date: May 16, 2006

(87) PCT Pub. No.: WO2004/046657

PCT Pub. Date: Jun. 3, 2004

(65) Prior Publication Data

US 2006/0259260 A1     Nov. 16, 2006

(30) Foreign Application Priority Data

Nov. 19, 2002 (DE) ................................ 102 54 053

(51) Int. Cl.
*G06F 15/00* (2006.01)
(52) U.S. Cl. ........................ 702/189; 702/182; 702/183; 702/184; 702/185; 702/186; 702/187; 702/188; 73/861.18
(58) Field of Classification Search ................ 702/189, 702/182–188; 73/61.79, 861.18
See application file for complete search history.

(56) References Cited

U.S. PATENT DOCUMENTS

| | | | |
|---|---|---|---|
| 4,122,713 A | 10/1978 | Stasz | |
| 6,209,388 B1* | 4/2001 | Letton et al. | 73/61.79 |
| 2002/0029130 A1* | 3/2002 | Eryurek et al. | 702/183 |

FOREIGN PATENT DOCUMENTS

| | | |
|---|---|---|
| DE | 2715876 | 11/1977 |
| DE | 19626865 | 1/1998 |
| DE | 19737394 | 3/1999 |
| DE | 19921984 | 11/2000 |
| DE | 19947992 | 5/2001 |
| WO | WO 9831989 | 7/1998 |

* cited by examiner

*Primary Examiner*—Marc S. Hoff
*Assistant Examiner*—Phuong Huynh
(74) *Attorney, Agent, or Firm*—Bacon & Thomas, PLLC

(57) ABSTRACT

A method and a device for determining and/or monitoring the volume flow rate and/or mass flow rate of a medium flowing through a container. In the case of the device, such is an ultrasonic flow measuring device, which works on the basis of the travel-time-difference principle. Additionally, a technique is presented whereby, on the basis of the results of measurement, also information is provided concerning change in some other system and/or process variable. To this end, the currently measured, actual measuring signals, or the corresponding actual measuring data, is compared with corresponding, stored set measuring signals, or set measuring data; a report is output, when a deviation arises between the set measuring signals, or set measuring data, and the actual measuring signals, or actual measuring data.

10 Claims, 4 Drawing Sheets

METHOD AND DEVICE FOR DETERMINING AND/OR MONITORING A VOLUME AND/OR MASS FLOW

FIELD OF THE INVENTION

The invention relates to a method for determining and/or monitoring the volume and/or mass flow of a medium flowing through a containment, wherein measuring signals are issued from an ultrasonic transducer placed in a first position on the containment and wherein the measuring signals are received by an ultrasonic transducer placed in a second position on the containment, and wherein, on the basis of the measuring signals, or on the basis of measuring data determined from the measuring signals, as the case may be, information is provided concerning the volume flow rate and/or the mass flow rate of the medium located in the containment. Usually, the containment is a pipe.

BACKGROUND OF THE INVENTION

Ultrasonic flow measuring devices are applied often in process and automation technology. They enable contactless determination of the volume and/or mass flow rate of a medium in a pipe.

The known ultrasonic measuring devices work either by the Doppler principle or the travel-time-difference principle. In the case of the travel-time-difference principle, the different travel time of the ultrasonic measuring signals in the direction of flow, and counter to the direction of flow, of the medium is exploited. To this end, the ultrasonic measuring signals are alternatingly issued, respectively received, in the direction of flow, and counter to the direction of flow, of the medium. On the basis of the travel-time-difference of the ultrasonic measuring signals, the flow velocity can be determined, and, with that and known diameter of the pipe, the volume flow rate of the medium, or, with known density, the mass flow rate of the medium.

In the case of the Doppler principle, ultrasonic measuring signals of known frequency are coupled into the flowing medium. The ultrasonic measuring signals reflected in the medium are evaluated. On the basis of a frequency shift occurring between the ultrasonic measuring signal which was coupled into the medium and the reflected ultrasonic measuring signal, likewise the flow velocity of the medium, or the volume and/or mass flow rate, can be determined. The use of flow measuring devices working according to the doppler principle are only possible, when are air bubbles or impurities are present in the medium, on which the ultrasonic measuring signals are reflected. Thus, the use of ultrasonic flow measuring devices using the Doppler principle is rather limited, compared to ultrasonic flow measuring devices using the travel-time-difference principle.

With respect to types of measuring devices, a distinction is drawn between ultrasonic flow measuring pickups, which are inserted into the pipeline, and clamp-on flow measuring devices, where the ultrasonic transducers are pressed onto the pipeline externally by means of a clamp. Clamp-on flow measuring devices are described, for example, in EP 0 686 255 B1, U.S. Pat. No. 4,484,478 or U.S. Pat. No. 4,598,593.

In the case of the two types of ultrasonic flow measuring devices, the ultrasonic measuring signals are radiated at a predetermined angle into, and/or received from, the pipe containing the flowing medium. In order to be able to radiate the ultrasonic measuring signals at determined angles into and out of the pipe, and into and out of the medium, as the case may be, the in- and out-coupling of the ultrasonic measuring signals into and out of the pipe occurs in the case of clamp-on flow measuring devices via interface pieces, or coupling wedges. In order to achieve an optimum impedance matching, it is, moreover, known to make the coupling wedges of a suitably refracting material, e.g. a synthetic material, or plastic. The principal component of an ultrasonic transducer is usually at least one piezoelectric element, which produces the ultrasonic measuring signals and/or receives them.

Now, there are different reasons why the measuring of volume, or mass, flow rate by means of ultrasonic measuring signals may fail. Generally, a bad measurement occurs, however, at least always when the sound path, on which the ultrasonic measuring signals propagate from the sending ultrasonic transducer, to the receiving ultrasonic transducer, gets interrupted at some location. Such an interruption can occur at various locations in the sound path. As examples, the following system and process defects can be mentioned:

The damping of the medium is too great;
the coupling of at least one ultrasonic transducer onto the containment is insufficient;
there is an air gap between the inner wall of the containment and a liner applied to the inner wall of the containment;
the damping in the material of the containment is too great; this can be the case e.g. when the ultrasonic measurement occurs in GFK (glass fiber reinforced plastic) pipes;
the containment, e.g. pipe, is empty—for some reason, there is no medium in the pipe.

It is desirable in this connection that the operating personnel not only be shown that a malfunction has occurred, but, also, where the real cause of the malfunction is to be sought. In the known flow measuring devices, the cause of an occurring malfunction, or the interruption of the sound path, must be determined in a more or less complicated, trial-and-error method. This is, naturally, involved and cost-intensive. Thus, it can happen, that the measuring device is subjected to an extensive examination, when, in fact, the bad measurement is being caused by an absence of medium flowing in the pipe.

SUMMARY OF THE INVENTION

An object of the invention is to provide a method and an device enabling, in addition to the determining of the volume, or mass, flow rate of a medium, the recognizing of a malfunction of some other system and/or process variable.

The object is achieved with respect to the method, in that currently measured, actual measuring signals, or corresponding actual measuring data, are compared with corresponding, stored, set measuring signals, or set measuring data, and that a report is issued, when a deviation arises between the set measuring signals or set measuring data and the actual measuring signals or actual measuring data. Preferably, a deviation between the set measuring signals or set measuring data and the actual measuring signals or actual measuring data is detected using a clamp-on flow measuring device working on the basis of the travel-time principle. The set measuring signals or the set measuring data or the signatures discussed below are stored in a memory unit in the form of tables and/or functions. The comparison between the set measuring signals or the set measuring data and the actual measuring signals or actual measuring data is done preferably by means of a correlation. The comparison of the current measuring signals/measuring data with a plurality of set measuring signals or set measuring data, which were determined under various, defect-burdened conditions, can be performed successively or in parallel. If at least a predetermined degree of similarity arises between the set measuring signals or set measuring data and the actual measuring signals or actual measuring data, for example if the correlation coefficient is exceeded or subceeded (fallen beneath) by a predetermined tolerance value, then the cause of the interruption of the sound path can be determined. This cause of the interruption of the sound path is specifically determined and output. The operating personnel can then handle the malfunction which has arisen, knowing what it is, without having to search long for the cause of the malfunction.

In an advantageous, further development of the method of the invention, it is provided that from each of the actual measuring signals or actual measuring data and the set measuring signals or set measuring data a signature is derived, with the information concerning the volume or mass flow rate of the medium being described sufficiently accurately by the signature. This procedure leads to a reduction of the measuring data, without its information content being impaired in its essential details. The reduction means that the computing power of the control/evaluation unit is reduced, especially in the case of the comparison of the set with the actual measuring signals/measuring data, i.e. less powerful microprocessors can be used. The same is true with respect to the memory chips needed for the application. It is to be noted that the energy requirement and the manufacturing costs can be significantly reduced by means of this embodiment of the method of the invention. In an embodiment of the method of the invention, the set measuring signals are preferably determined both for the case of not filled containment and for the case of filled containment.

A preferred form of embodiment of the method of the invention provides that: The actual measuring signals or the set measuring signals and/or the corresponding signatures are digitized and stored; the actual measuring signals/actual measuring data or the signatures determined on the basis of the actual measuring signals/actual measuring data are compared with the corresponding set measuring signals/set measuring data or the corresponding signatures of the set measuring signals/measuring data; an error report is output to the operating personnel with specific indication as to the cause for the arisen error, as soon as a deviation between the actual and set measuring signals/measuring data or the actual and set signatures occurs; preferably, the error report is first output, when the deviation lies outside of a predetermined tolerance value. Parallel to the error report, also direct correction- and counter-measures can be instituted by means of the control/evaluation unit. Such measures include e.g. the checking of valves, the instituting of a cleaning process or an emergency shutdown of the process plant.

Furthermore, an advantageous embodiment of the method of the invention provides that, on the basis of the comparison of the actual measuring signals/actual measuring data or on the basis of the comparison of the signatures of the actual measuring signals/actual measuring data with the set measuring signals/set measuring data or the corresponding signatures of the set measuring signals/set measuring data, a statement can be made as to which system and/or process defect is causing the deviation. A significant source of error is—as already mentioned—the interruption of the sound path taken by the ultrasonic measuring signals from the emitting, to the receiving, ultrasonic transducer. By the embodiment of the invention, it is now possible to perform a so-called advanced diagnostic, i.e. to not only indicate to the operating personnel that somewhere in the measuring device or in the process a malfunction has arisen, but also to provide specific information as to the cause of such malfunction.

For example, it is recognized, on the basis of the deviation, that the containment is not filled with the medium, and/or that the coupling of the ultrasonic transducer onto the containment is faulty, and/or that the damping of the measuring signals by the medium located in the containment exceeds a predetermined maximum value, and/or that an air gap is present between the containment and a liner applied to the inner surface of the containment, and/or that the damping of the measuring signals in the wall of the containment exceeds a maximum predetermined amount. Thus, the operating personnel are not only told that a system and/or process malfunction has arisen, but also are given a reliable indication of where the malfunction is located. Without great time delay and complex investigations, repair and/or countermeasures can be directed right to the source of the problem.

In general, the following can be stated: In order to be able to compare the set data and the actual date, the set data are recorded and stored for empty pipe, before the actual measuring operation. In this way, the device is "taught" how the ultrasonic measuring signals look for the case of empty pipe. In the actual measuring operation of the ultrasonic flow measuring device, the stored set data is not of interest in terms of measurement results. Only in the case of error, thus when the acoustic measuring path is interrupted, are the actual measuring data compared with the stored, set data. If the data are essentially the same, then the statement can be made that the pipe is, with high probability, empty. If the data do not agree sufficiently, then, evidently, another reason is the basis for the interruption of the acoustic sound path and the associated bad measurement. By a method of successive comparisons, the cause of the malfunction can subsequently be ascertained and, in the end, reliable statements made concerning the cause of the malfunction.

With respect to the device, the object is achieved by a control/evaluation unit which compares the actual measuring signals or the corresponding actual measuring date with corresponding, stored, set measuring signals or set measuring data, and outputs a deviation between the set measuring signals or set measuring data and the actual measuring signals or actual measuring data.

An advantageous embodiment of the device of the invention provides that the control/evaluation unit presents information concerning which system and/or process defect or malfunction is causing the deviation.

Preferably, the ultrasonic transducer is arranged as a one-traverse arrangement or as a multi-traverse arrangement. A traverse here is the portion of a sound path in which an ultrasonic measuring signal crosses the containment, in which the measurement is being conducted, once. Besides diametral traverses, appropriate transducer arrangement—perhaps with the help of reflector elements—permits, in simple manner, also the realization of chordal traverses.

Preferred is the use of an embodiment of the device of the invention, wherein at least the two ultrasonic transducers having the greatest separation from one another operate alternatingly in emitting and receiving modes. As already stated, the ultrasonic transducers are preferably—although not exclusively—mounted on the containment using the clamp-on method.

BRIEF DESCRIPTION OF THE DRAWINGS

The invention will now be explained in greater detail on the basis of the appended drawings, the figures of which show as follows.

DESCRIPTION OF THE PREFERRED EMBODIMENTS

Figure 1:
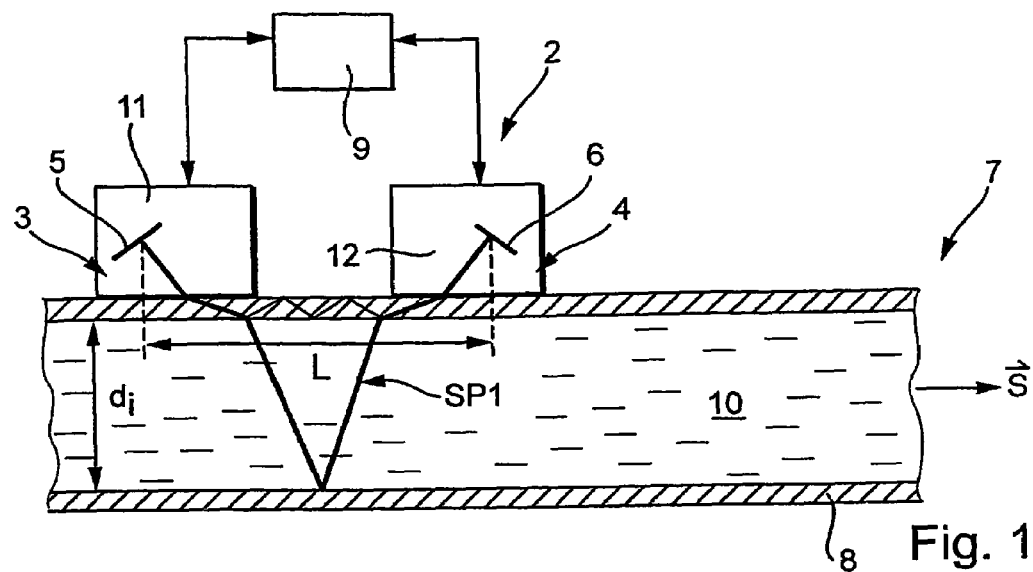
FIG. 1 a clamp-on flow measuring device, in a two-traverse arrangement.

FIG. 1 is a schematic presentation of a clamp-on flow measuring device in the preferred, two-traverse arrangement 2. The measuring device determines volume flow rate, and/or mass flow rate, of the medium 10 in the pipe 7 using the known travel-time-difference method.

Essential components of the clamp-on ultrasonic flow measuring device are the two ultrasonic transducers 3, 4 and the control/evaluation unit 9. The two ultrasonic transducers 3, 4 are secured on the wall 8 of the pipe 7 by means of a securement device not separately shown in FIG. 1. Appropriate securement devices are well known from the state of the art and are also available from Endress + Hauser. The medium 10 flows through pipe 7 of predetermined inner diameter $d_i$ in the stream direction S.

An ultrasonic transducer 3, 4 includes, as essential components, at least one piezoelectric element 5, 6, which produces and/or receives the ultrasonic measuring signals, and a coupling wedge, or interface piece, 11, 12. The ultrasonic measuring signals are coupled into, and out of, the pipe 7 containing the flowing medium 10 via the coupling wedges 11, 12. The coupling wedges 11, 12 determine the entering and exiting directions of the ultrasonic measuring signals relative to the pipe and medium. Additionally, the wedges can serve to optimize impedance matching.

The two ultrasonic transducers 3, 4 are positioned on the wall 8 of the pipe 7 in such a way that a high fraction of the emitted ultrasonic measuring signals is received in the respective other ultrasonic transducer 3, 4. The positioning of the transducers, one with respect to the other, is a function of different system and/or process variables, such as the inner diameter di of the pipe 7, the thickness w of the pipe wall 8, the velocity of sound cP in the material of which the pipe 7 is made, or the velocity of sound cM in the medium 10.

In the illustrated case, the separation L of the two ultrasonic transducers 3, 4 is selected such that the ultrasonic measuring signals, which, in keeping with the travel-time-difference method, are issued and received alternatingly by the two ultrasonic transducers 3, 4, propagate via the sound path SP1 in the pipe 7 containing the flowing medium 10. The sound path SP1 exhibits two traverses.

Figure 2:
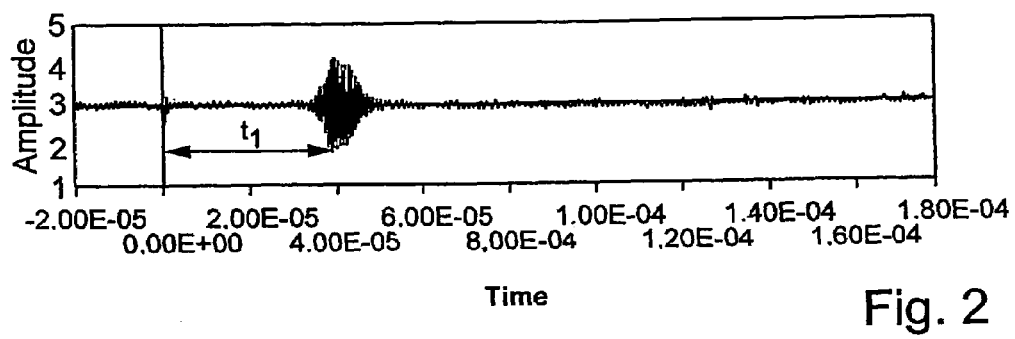
FIG. 2 a graphical representation of travel time of an ultrasonic measuring signal in the two-traverse arrangement shown in FIG. 1, for the case of empty pipe.
Figure 3:
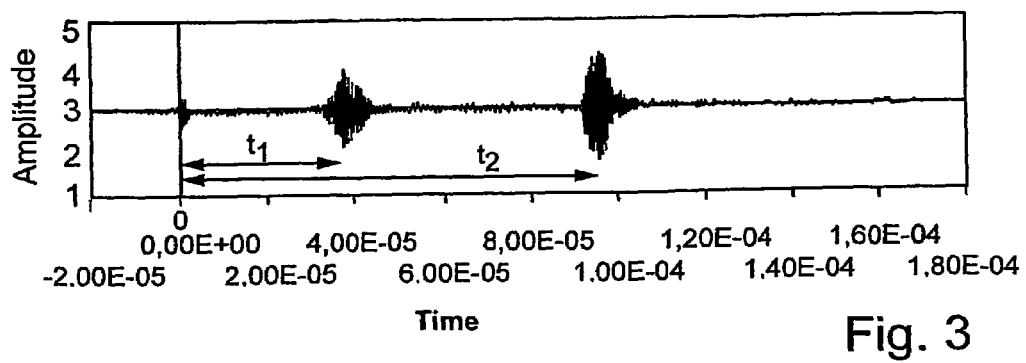
FIG. 3 a graphical representation of travel time of an ultrasonic measuring signal in the two-traverse arrangement shown in FIG. 1, for the case of filled pipe.

The diagrams of FIGS. 2 and 3 illustrate amplitude versus time for the ultrasonic measuring signals propagating in the pipe wall 8 and—when present—in the medium 10. Reference is made to FIG. 1 and its two-traverse arrangement 2 of the ultrasonic transducers 3, 4. FIG. 2 is for the case of "malfunction", wherein the pipe 7 is empty, while FIG. 3 shows the "normal" case, in which the medium 10 is flowing through the pipe 7. At least the information concerning the case of "malfunction", preferably, however, also the information concerning the "normal" case, must be stored in some form in the control/evaluation unit 9 as the set value.

In the case of an empty pipe 7, the ultrasonic measuring signal has, as can be seen from FIG. 1, only the possibility of propagating via the pipe wall 8. An ultrasonic measuring signal emitted at time "zero" from the first ultrasonic transducer 3 is received following a time t1 by the second ultrasonic transducer 4. The travel time of the ultrasonic measuring signal can either be measured or calculated. A calculation of the travel time is possible at least to an approximation, when the geometric data ($d_i$ and w) of the pipe and the acoustic properties of the pipe and medium ($c_P$ and $c_M$) are known. Snell's Law is used for the calculation.

Additionally, a corresponding measurement can be performed e.g. when the ultrasonic measuring device is first installed, which is then the set measuring signal for an empty pipe. If the corresponding case is noted sometime after installation of the ultrasonic measuring device, then, on the basis of the match found by the control/evaluation unit 9 between the actual measuring signal and the set measuring signal, a clear statement can be made, that no medium 10 is present in the pipe 7.

If medium is flowing through the pipe 7, then the largest part of the ultrasonic measuring signal emitted by one of the two ultrasonic transducers 3, 4 is coupled into the medium 10 and reaches the other ultrasonic transducer over the sound path SP1, which crosses the pipe 7, and, consequently, the flowing medium, two times. Due to the longer travel distance on the sound path SP1, an ultrasonic measuring signal is, as can be seen in FIG. 3, only received in the other ultrasonic transducer after the longer period of time $t_2$. To be added into these considerations is that, in many applications, the sound velocity is lower in the medium 10 than it is in the material of the pipe wall 8. Also this contributes to a delayed arrival of the measuring signal containing information concerning the volume, or mass, flow rate of the medium 10 in the pipe 7.

Figure 4:
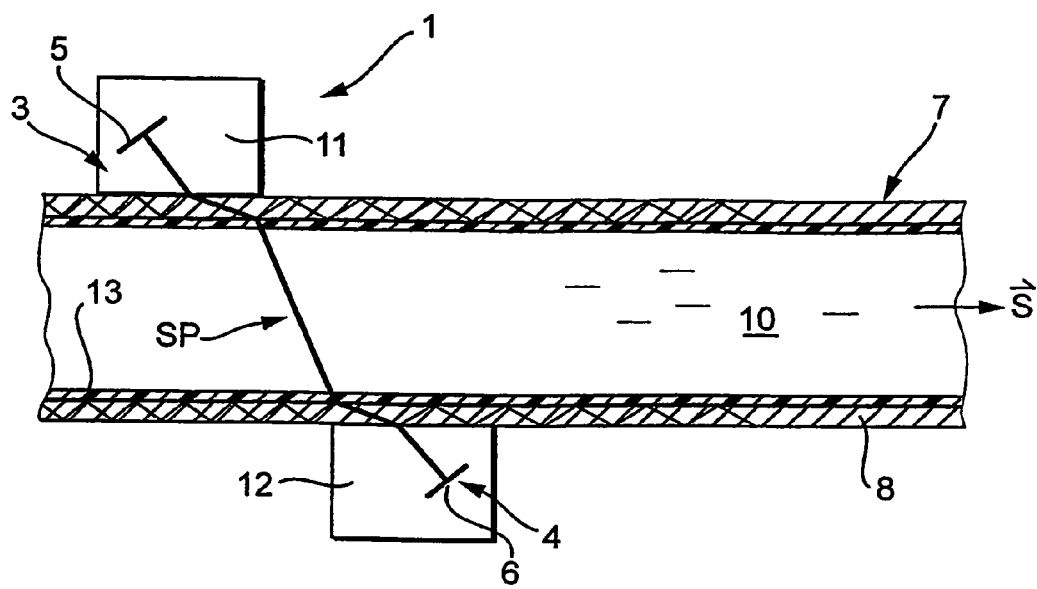
FIG. 4 a clamp-on flow measuring device, in a one-traverse arrangement.

FIG. 4 shows schematically a clamp-on flow measuring device in a one-traverse arrangement 1. The measuring device determines the volume, and/or mass, flow rate of the medium 10 in the pipe 7 likewise according to the known travel-time-difference method. In this case, the two ultrasonic transducers 3, 4 are placed on opposite sides of the pipe 7, displaced with resect to one another. In turn, the ultrasonic transducers are positioned such that as large a fraction as possible of an ultrasonic measuring signal emitted from a first ultrasonic transducer 3, 4 is received in the other ultrasonic transducer 3, 4.

Figure 5:
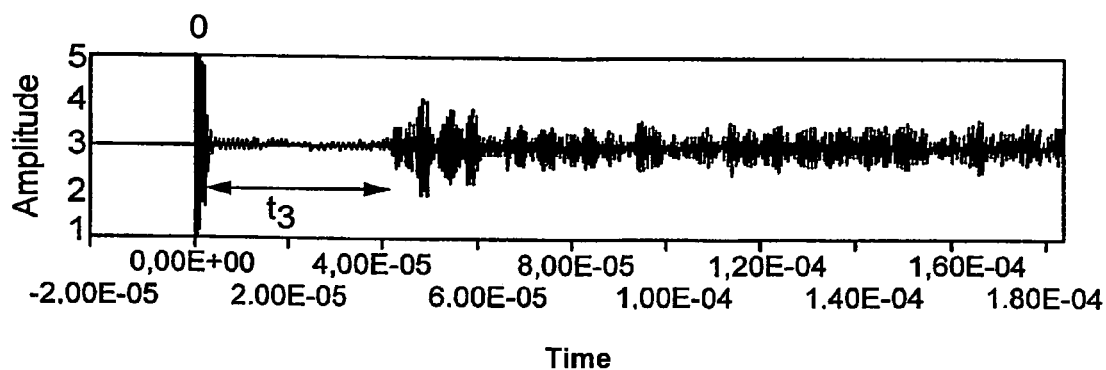
FIG. 5 a graphical representation of travel time of an ultrasonic measuring signal in the one-traverse arrangement shown in FIG. 4, for the case of empty pipe.
Figure 6:
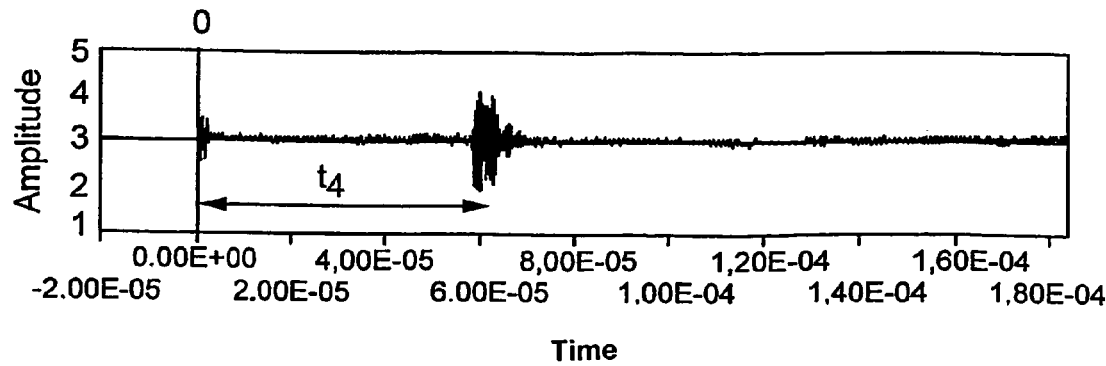
FIG. 6 a graphical representation of travel time of an ultrasonic measuring signal in the one-traverse arrangement shown in FIG. 4, for the case of filled pipe.

FIGS. 5 and 6 show in two diagrams, the amplitudes of the ultrasonic measuring signals propagating in the pipe wall 8 as a function of time, and, when present, in the medium 10. Reference is now made to the one-traverse arrangement 1 of the ultrasonic transducers 3, 4 shown in FIG. 4. While FIG. 5 shows the case of "malfunction", where pipe 7 is empty, FIG. 6 presents the "normal" case, in which medium 10 is flowing through the pipe 7. Also in this arrangement of the ultrasonic transducers 3, 4, at least the information concerning the case of "malfunction", preferably, however, also concerning the "normal" case, must be stored in some form in the control/evaluation unit 9 as the set value.

In the case of empty pipe 7, an ultrasonic measuring signal can only propagate via the pipe wall 8. Consequently, an ultrasonic measuring signal emitted from the first ultrasonic transducer 3, 4 shows itself in the second ultrasonic transducer as a noisy signal, as can be seen in FIG. 5. The time $t_3$, which passes before the emitted ultrasonic measuring signal is received, is, in turn, determined by the separation of the ultrasonic sensors 3, 4 and by the velocity of sound in the material of the pipe 7.

In the case of a filled pipe 7, an emitted measuring signal is received in the other ultrasonic transducer following a length of time t4. Also here, a comparison e.g. of the actual measuring signals with the set measuring signals permits an unequivocal decision as to whether the pipe 7 is filled with medium 10 or empty. As already mentioned, preferably a correlation is performed for the purpose of comparison. If the correlation coefficient between the set data and the actual data subceeds (falls below) or exceeds a predetermined value, then the report is issued indicating the specific malfunction.

Figure 7:
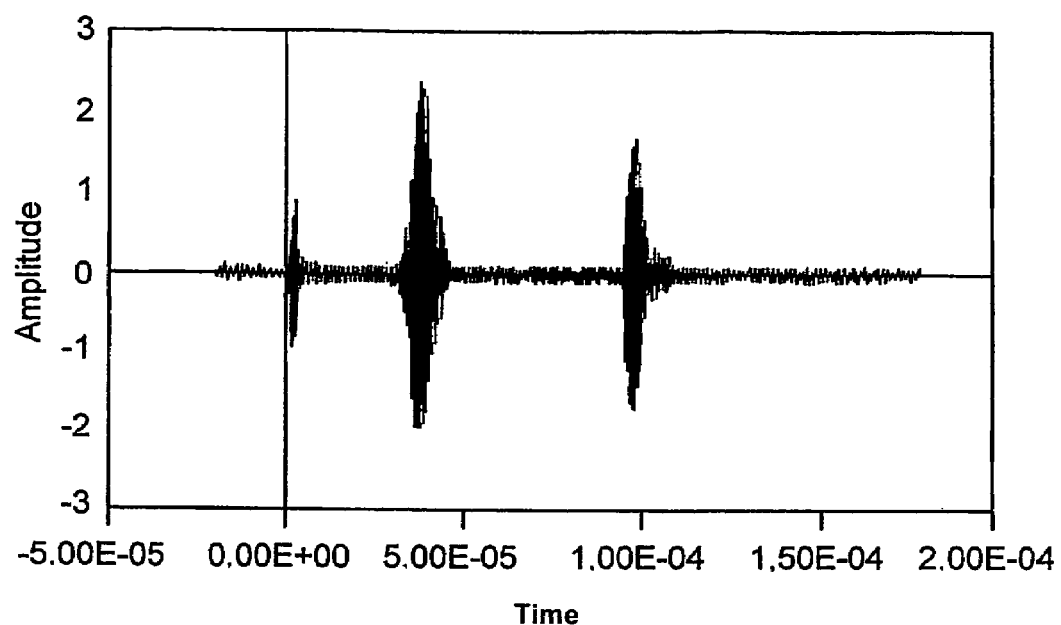
FIG. 7 a graphical representation of travel time of an ultrasonic measuring signal in the two-traverse arrangement shown in FIG. 1, for the case of correct coupling of the ultrasonic transducers to the pipe.
Figure 8:
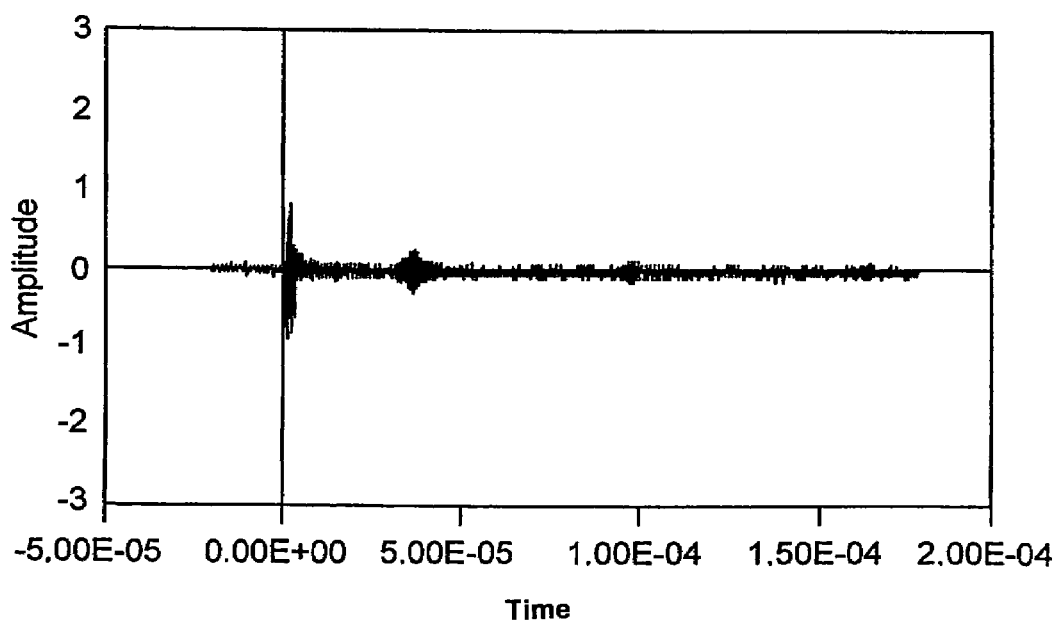
FIG. 8 a graphical representation of travel time of an ultrasonic measuring signal in the two-traverse arrangement shown in FIG. 1, for the case of defective coupling of the ultrasonic transducers to the pipe.

FIGS. 7 and 8 likewise show graphical presentations of the travel time of ultrasonic measuring signals for the two-traverse arrangement 2 illustrated in FIG. 1. The first peak corresponds to the fraction of the measuring signals, which propagate via the pipe 7, while the second peak represents the fraction of the ultrasonic measuring signals propagating via the medium 10. FIG. 7 shows ultrasonic measuring signals, as they occur for the case of undisturbed, normal, measuring operation. FIG. 8 relates to the case where the coupling wedges 11, 12 are largely removed from the pipe 7, so that there is only very little sound transmission between the ultrasonic transducers 3, 4 and the pipe 7. Thus, also in this case, the sound path is interrupted. One can see in FIG. 8 that the amplitudes of the two ultrasonic measuring signals become proportionately smaller compared to the normal measuring operation. This characterizing property can now be used even for distinguishing whether the damping of the measuring signals is a result of poor coupling of the ultrasonic transducers 3, 4 onto the pipe 7 or the result of strong damping by the pipe 7/medium 10 arrangement. In the extreme case, when the coupling is completely interrupted, no measuring signal can any longer be seen. Neither the measuring signal propagating via pipe 7 (first peak in FIG. 7) nor the measuring signal propagating via the medium 10 (second peak in FIG. 7) can be measured.

Figure 9:
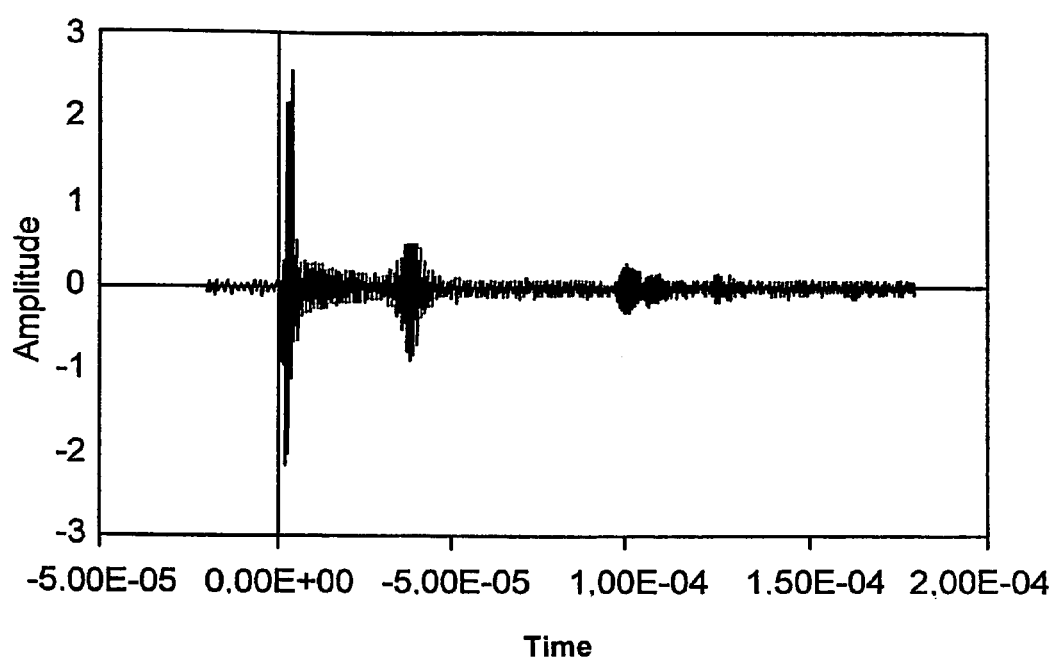
FIG. 9 a plot of the ultrasonic measuring signals of FIG. 8, with greater amplification factor.

FIG. 9 shows the same signal plot as shown in FIG. 8, but amplified in FIG. 9 by a factor of about 4. This separates the real measuring signals better from the noise.

In the case of the previously described embodiment, which allows recognition of an insufficient coupling of the ultrasonic transducers 3, 4 on the pipe 7, the following manner of proceeding is advantageous for the evaluation of the ultrasonic measuring signals: The set data are recorded following installation of the clamp-on flow measuring device during normal operation. Then, the actual data is continuously compared with the set data. If it is found on the basis of a comparison of the set data with the actual data, that the amplitudes of the measuring signals, which propagate via the medium 10, fade more strongly over time than the amplitudes of the measuring signals, which propagate via the pipe 7, then this is an unequivocal indication that the malfunction lies in the transmission in the pipe 7/medium 10 arrangement. In contrast, if the amplitudes of both measuring signals decrease, then this is a clear indication that the coupling between an ultrasonic transducer 3, 4 and the pipe 7 has degraded. In general, it can be said that, best suited for recognizing a defect in the pipe 7/medium 10 coupling or in the coupling between ultrasonic transducers 3, 4 and pipe 7 is a change of the amplitude ratios between the measuring signals.

The inventions claimed is:

1. A method for determing and/or monitoring the volume flow rate of a medium flowing in a containment, comprising the steps of:
    measuring signals are emitted from an ultrasonic transducer placed in a first position on the containment;
    receiving the measuring signals by an ultrasonic transducer placed in a second position on the containment;
    providing information on the basis of the measuring signals, or on the basis of measuring data obtained from the measuring signals, concerning the volume flow rate of the medium located in the containment;
    comparing the currently measured, actual measuring signals, or the corresponding actual measuring data with corresponding, stored, set measuring signals, or set measuring data; and
    issuing a report, when a deviation arises between the set measuring signals, or set measuring data, and the actual measuring signals, or actual measuring data, wherein:
    on the basis of the deviation, at least one of the following is recognized:
    the containment is not filled with the medium,
    the coupling of the ultrasonic transducers to the containment is defective,
    the damping of the measuring signals by the medium located in the containment exceeds a predetermined maximum value,
    an air gap between the containment and a liner on the inner surface of the containment is present, and
    the damping of the measuring signals in the wall of the containment exceeds a maximum, predetermined amount.

2. The method as claimed in claim 1, further comprising the step of:
    deriving signatures from the actual measuring signals, or actual measuring data, and from the set measuring signals, or set measuring data, wherein the signatures describe each of the measuring signals sufficiently accurately.

3. The method as claimed in claim 1, wherein:
    the set measuring signals are determined for not-filled containment and/or for filled containment.

4. The method as claimed in claim 1, further comprising the steps of:
    digitizing and storing the actual measuring signals, or set measuring signals, and/or the corresponding signatures;
    comparing the actual measuring signals/actual measuring data, or the signature determined from the actual measuring signals/actual measuring data, with the corresponding set measuring signals/set measuring data or the corresponding signature of the set measuring signals/measuring data; and issuing a report, when a deviation arises between the actual and set measuring signals/measuring data, or between the actual and set signatures, which lies outside of a predetermined tolerance value.

5. The method as claimed in claim 4, further comprising the step of:

making a statement on the basis of the comparison of the actual measuring signals/actual measuring data, or on the basis of the comparison of the signatures of the actual measuring signals/actual measuring data, with the set measuring signals/set measuring data, or the corresponding signatures of the set measuring signals/set measuring data, as to which defective system and/or process variable is causing the deviation.

6. A device for determining and/or monitoring the volume flow rate of a medium in a containment, comprising:

at least two ultrasonic transducers, wherein a first ultrasonic transducer is provided in a first position on the containment and wherein a second ultrasonic transducer is provided in a second position on the containment; and a control/evaluation unit, which determines the volume flow rate of the medium located in the containment on the basis of measuring signals delivered by said ultrasonic transducers, or on the basis of the corresponding measuring data, wherein:

said control/evaluation unit compares the currently measured, actual measuring signals, or the corresponding actual measuring data, with corresponding, stored set measuring signals, or set measuring data, and outputs a deviation between the set measuring signals, or set measuring data, and the actual measuring signals, or actual measuring data, wherein:

on the basis of the deviation, at least one of the following is recognized:

the containment is not filled with the medium, the coupling of the ultrasonic transducers to the containment is defective, the damping of the measuring signals by the medium located in the containment exceeds a predetermined maximum value, an air gap between the containment and a liner on the inner surface of the containment is present, and the damping of the measuring signals in the wall of the containment exceeds a maximum, predetermined amount.

7. The device as claimed in claim 6, wherein:

said control/evaluation unit provides information concerning which defective system, and/or process, variable is causing the deviation.

8. Device as claimed in claim 6, wherein:

the arrangement of said ultrasonic transducers is a one-transverse arrangement or a multi-traverse arrangement.

9. Device as claimed in claim 6, wherein:

said at least two ultrasonic transducers having the greatest separation from one another work alternatingly in emitting and receiving operation.

10. Device as claimed in claim 6, wherein:

said at least two ultrasonic transducers are mounted on the containment according to the clamp-on method.

* * * * *